United States Patent [19]

Murtha

[11] 4,174,302
[45] Nov. 13, 1979

[54] CATALYST FOR PRODUCTION OF CYCLOALKYLAROMATICS

[75] Inventor: Timothy P. Murtha, Bartlesville, Okla.

[73] Assignee: Phillips Petroleum Company, Bartlesville, Okla.

[21] Appl. No.: 933,343

[22] Filed: Aug. 14, 1978

Related U.S. Application Data

[62] Division of Ser. No. 608,597, Aug. 28, 1975, Pat. No. 4,115,463.

[51] Int. Cl.$^2$ .......................... B01J 29/06; B01J 29/12
[52] U.S. Cl. ................................. 252/455 R; 252/460
[58] Field of Search ............................. 252/460, 455 R

[56] References Cited

U.S. PATENT DOCUMENTS

| | | | |
|---|---|---|---|
| 2,918,509 | 12/1959 | Miller et al. | 252/460 X |
| 3,956,183 | 5/1976 | Zuech | 252/460 X |

Primary Examiner—Carl Dees

[57] ABSTRACT

Cycloalkylaromatics are produced from aromatic hydrocarbons in the presence of hydrogen and a catalyst consisting essentially of ruthenium, nickel and a support material selected from the group consisting of active clay and silica-alumina.

6 Claims, No Drawings

CATALYST FOR PRODUCTION OF CYCLOALKYLAROMATICS

This is a divisional of application Ser. No. 608,597, filed Aug. 28, 1975, now U.S. Pat. No. 4,115,463.

This invention relates to the conversion of aromatic hydrocarbons to cycloalkylaromatics and/or alkyl-substituted cycloalkylaromatics. In one aspect, this invention relates to an improved process for the conversion of aromatics to cycloalkylaromatics. In another aspect, this invention relates to an improved catalyst for the conversion of aromatics to cycloalkylaromatics.

Methods are available in the art for the coupling of aromatic nuclei in the presence of molecular hydrogen to produce an at least partially hydrogenated dimer derivative of the aromatic reactant. For example, benzene is converted at an elevated temperature to a mixture containing cyclohexylbenzene in the presence of various catalysts. Cyclohexylbenzene is known as a valuable solvent and chemical intermediate. It can be converted in high yield to phenol and cyclohexanone by autooxidation with subsequent acid treatments. None of the prior art methods have yet been proven for a stable continuous operation necessary for commercial exploitation. Problems therewith include high catalyst cost, catalyst stability, and regeneration.

An object of the present invention is to provide an improved process for the conversion of aromatic hydrocarbons to cycloalkylaromatic hydrocarbons.

Another object of the present invention is to provide an improved catalyst for the production of cycloalkylaromatic hydrocarbons.

Other objects, aspects and the several advantages of the invention will be apparent to those skilled in the art upon reading the specification and appended claims.

In accordance with the present invention there is provided a process for producing cycloalkylaromatics and alkyl-substituted cycloalkylaromatics from aromatic hydrocarbons by contacting a monocyclic aromatic hydrocarbon with hydrogen in the presence of a catalyst consisting essentially of ruthenium, nickel and a solid support material selected from the group consisting of active clay and synthetic silica-alumina under conditions sufficient to convert the monocyclic aromatic hydrocarbons to cycloalkylaromatics and alkyl-substituted cycloalkylaromatics, and thereafter recovering the desired product.

The present process is effected in the presence of a clay-supported or a silica-alumina-supported ruthenium/nickel catalyst. The ruthenium and nickel are applied to the active clay or synthetic silica-alumina support material as alcoholic or aqueous solutions of a ruthenium halide salt, preferably ruthenium trichloride, and nickel bromide, such as nickel dibromide trihydrate.

The catalyst preparation involves no calcination but simply involves the impregnation of the active clay or silica-alumina with a solution containing ruthenium and nickel, such as an ethanol or water solution of ruthenium trichloride and nickel bromide trihydrate. The impregnation of the support material with the ruthenium and nickel compounds can be carried out simultaneously with a single impregnating solution or sequentially with separate solutions. The amount and concentration of the impregnating solution should be sufficient to provide the desired ruthenium and nickel concentrations in the finished catalyst.

Following impregnation the catalytic composite is dried to remove the volatile solvent at atmospheric pressure or at reduced pressure. The catalytic composite can be further dried by heating at temperatures in the approximate range of 25° to 380° C., preferably from 25° to 120° C. The heating is continued for a period of time and under conditions sufficient to remove substantially all of the solvent but insufficient to calcine the catalyst composition.

The catalytic composite can be used in the powder form or as tablets. Tablets of the support material can be prepared and impregnated with ruthenium and nickel, or the powder can be impregnated and then converted to tablets. In the preparation of tablets it is advantageous to incorporate about three weight percent graphite as a processing aid. It is desirable that the tablets have a crush strength of 5-10 pounds.

The catalysts of this invention contain ruthenium and nickel in the following amounts:

|  | Broad | Preferred |
|---|---|---|
| Ruthenium, wt. % | 0.01–0.3 | 0.03–0.1 |
| Nickel, wt. % | 0.03–1.0 | 0.1–0.6 |
| Ru:Ni (w/w) | 0.01:1–0.3:1 | 0.1:1–0.25:1 |

The above weight percents are based upon the weight of the support material and are calculated as the metal.

After impregnation and drying, the catalyst composite is ready for use in the process of this invention. However, it is generally advantageous to treat the catalyst prior to contact with the aromatic feedstock by flowing hydrogen over the catalyst for 0.1–10 hours at 100°–275° C.

As indicated above, the support material for the catalyst of this invention is an activated clay or a synthetic silica-alumina. Good results are obtained when a support characterized by montmorillonite structure is impregnated with an alcoholic or aqueous solution of ruthenium trichloride and nickel dibromide trihydrate followed by heating to remove the solvent. Suitable clays are available commercially, as for example, Filtrol Grade 71, Filtrol Grade 49 and the like (available from Filtrol Corporation, Vernon, Calif. A typical analysis of the Filtrol Grade 71 clay is as follows: 71.2% $SiO_2$, 16.5% $Al_2O_3$, 3.6% $Fe_2O_3$, 3.2% MgO, 2.6% CaO, 1.3% $SO_3$, 1.0% ($K_2O+Na_2O$) and 0.6% $TiO_2$ (analysis on a volatile free basis). Filtrol Grade 49 clay has the following analysis: 74.0% $SiO_2$, 17.5% $Al_2O_3$, 4.5% MgO and 1.4% $Fe_2O_3$ with the balance not specified by Filtrol Corp. Filtrol Grade 49 was analyzed by the supplier after heating the Filtrol sample at 1700° F. In this heat treatment Filtrol Grade 49 lost 17% volatiles.

In addition to the montmorillonite clays, other catalyst grade synthetic silica-alumina materials, containing a major proportion of silica and a minor proportion of alumina, i.e., at least about 50 weight percent silica, can be used in the preparation of the catalysts of this invention. Particularly effective are the acidic synthetic silica-aluminas having activity as cracking catalysts. An example of such a support material is Durabead silica-alumina, available commercially from Mobile Chemical Co., 150 East 42nd St., N.Y., N.Y. 10017.

The feedstocks which are suitable for use in the present invention are monocyclic aromatic or alkyl-substituted monocyclic aromatic compounds having from 6 to 10 carbon atoms per molecule. Examples of suitable aromatic compounds include benzene, toluene, the xylenes, isobutylbenzene and the like, and mixtures thereof.

The aromatic conversion according to the present invention can be carried out in the presence of the above-described catalysts at a temperature in the approximate range of 100°–275° C., preferably 185°–250° C. When using a catalyst prepared from active clay support materials, a reaction temperature less than about 220° C., preferably in the range of 190°–215° C., is preferred for best results. When using a catalyst prepared from a synthetic silica-alumina support material a reaction temperature above about 225° C., preferably 225°–230° C., is preferred for best results.

The aromatic conversion is carried out at a hydrogen pressure in the approximate range of 100 to 2000 psig, preferably from 400 to 600 psig.

The present invention can be carried out batchwise or as a continuous process. Continuous operation is more suitable for commercial utilization. In a continuous process, the aromatic hydrocarbon-hydrogen feed can be passed over a fixed bed catalyst in an upflow or downflow manner. In a continuous operation the feedstock is contacted with the catalyst at a space velocity, defined as volume of the liquid feed per volume of catalyst per hour (LHSV), in the approximate range of 1 to 45, preferably 20–35.

The present invention is advantageously carried out under substantially anhydrous conditions.

The process of this invention can be carried out in the presence of or in the substantial absence of added reaction solvents or diluents. In the modification wherein added solvent is employed, the diluents which are liquid at reaction temperature and pressure and are inert to the catalyst, reactants and reaction products are suitably employed. Preferred diluents to be utilized in this modification are saturated hydrocarbons of 5–10 carbon atoms, e.g., acyclic alkanes such as pentane, hexane, heptane, octane, nonane and decane, as well as cycloalkanes, such as cyclopentane, cyclohexane, cycloheptane, cyclooctane, cyclononane, cyclodecane and the like and mixtures thereof. The presently preferred diluent is cyclohexane.

The desired product can be isolated and recovered by any convenient means such as by fractionation. The unconverted feedstock can be recycled to the reaction zone.

In a presently preferred embodiment of the invention, benzene, preferably containing little if any sulfur, is contacted at a temperature in the approximate range of 185° to 250° C., at a LHSV in the approximate range of 20–35 and under a hydrogen pressure in the approximate range of 400–600 psig with a catalyst consisting essentially of ruthenium and nickel on an active clay or silica-alumina support, which catalyst has been prepared by impregnating the support with an ethanolic solution of a ruthenium halide and nickel bromide followed by heating to remove the solvent (ethanol) under non-calcining conditions at a temperature below about 380° C., but sufficient to volatilize and remove the ethanol from the impregnated catalyst. Cyclohexylbenzene is recovered from the reaction mixture.

The following examples illustrate the invention:

EXAMPLE I

(A) Catalyst Preparation

Twenty-five grams of Filtrol Grade 49, 20–30 mesh, which had been previously heated at 293° C. for two hours, was impregnated with about 80 ml of an ethanolic solution containing 0.0309 g. ruthenium trichloride and 0.2024 g. nickel chloride hexahydrate. The ethanol was removed under reduced pressure on a rotary evaporator and the catalyst was dried overnight at room temperature. The resulting catalyst was calculated to contain 0.05 weight percent Ru and 0.20 weight percent Ni.

(B) Cyclohexylbenzene Run 1

A $\frac{3}{8}''\times 18''$ stainless steel pipe downflow trickle bed reactor was charged with 25 ml Pyrex glass beads followed by 15 ml (10.9 g.) of the above catalyst and topped by additional Pyrex glass beads to give a total charged volume of about 25 ml. The system was pressure checked, heated to 150° C., and pressured to 500 psig with hydrogen for 15 minutes. During a reaction period of four hours, benzene was pumped into the stainless steel tube reactor at a rate of 300 ml/hr (LHSV=20) at a hydrogen pressure of 500 psig and a temperature of 215° C. The reactor effluent was collected in a receiver which was changed at approximately one hour intervals, and the composition of each sample was determined by gas chromatographic analysis. The gas chromatographic analyses of samples taken during the last four hours of a run were averaged and the results showed a 1.4% conversion based on benzene, with a selectivity of 62% to cyclohexylbenzene and 19% to cyclohexane. The ratio of cyclohexylbenzene/cyclohexane (CHB/CH) was 3.3.

EXAMPLE II

(A) Catalyst Preparation

Twenty-five grams of Filtrol Grade 49, 20–30 mesh, which had been previously heated at 293° C. for two hours was sprayed with a solution containing about 30 ml absolute ethanol, 3 ml water, 0.0309 g. ruthenium trichloride and 0.2315 g. nickel bromide trihydrate. The catalyst was air dried overnight at room temperature. The resulting catalyst was calculated to contain 0.05 weight percent Ru and 0.20 weight percent Ni.

(B) Cyclohexylbenzene Run 2

A charge of 15 ml (12.2 g) of the above catalyst was placed in a stainless steel pipe reactor ($\frac{3}{8}''\times 18''$) bedded with Pyrex glass beads. The system was pressure checked, purged with nitrogen and hydrogen before treating the catalyst at 150° C. under 500 psig H$_2$ for a period of 15 minutes. Benzene was then pumped into the reactor at a rate of 300 ml/hr (LHSV=20) during a reaction period of seven hours at about 210° and a hydrogen pressure of 500 psig. The gas chromatographic analyses of samples taken over the seven hour reaction period were averaged and the results showed a 14% conversion based on benzene with a selectivity of 9.5% to cyclohexane and 76.7% to cyclohexylbenzene. The CHB/CH ratio for this run was 8.1.

The results shown in Table I below illustrate that the Runs of Examples I and II, in which the catalysts contain relatively small amounts of ruthenium, both produced significant amounts of the desired cyclohexylbenzene. In addition, it is also clearly seen that the catalyst prepared using NiBr$_2$ is much superior to that using NiCl$_2$.

Table I

| | Production of Cyclohexylbenzene | | | | | |
|---|---|---|---|---|---|---|
| Ex. No. | Components, wt. % Ru | Ni | Temp. °C. | LHSV | % Conversion | CHB Sel. % | Ratio CHB/CH |
| I | 0.05 | 0.20[a] | 215 | 20 | 1.4 | 62 | 3.3 |
| II | 0.05 | 0.20[b] | 210 | 20 | 14.0 | 76.7 | 8.1 |

[a]Ni present as NiCl$_2$.
[b]Ni present as NiBr$_2$.

EXAMPLE III

(A) Catalyst Preparation

A 25 g. sample of Filtrol Grade 71 was sprayed with a solution containing about 20 ml ethanol, 1 ml water, 0.0309 g. ruthenium trichloride and 0.2315 nickel bromide trihydrate. The catalyst was air dried overnight at room temperature. The resulting catalyst was calculated to contain 0.05 weight percent Ru and 0.20 weight percent Ni.

(B) Cyclohexylbenzene Run 3

A 15 ml (9.7 g.) portion of the above catalyst (0.05 wt. % Ru, 0.20 wt. % Ni on Filtrol Grade 71) was placed in the stainless steel tubular reactor of Example I bedded with Pyrex glass beads. The reactor was pressure checked and purged with nitrogen before pressuring to 500 psig H$_2$ and heating to 150° C. over a period of 15 minutes. Benzene was pumped into the reactor at a rate of 300 ml/hr (LHSV=20) and a five hour run was carried out at a pressure of about 500 psig H$_2$ and at a temperature of about 200° C. The gas chromatographic analyses of samples taken during the five hour run were averaged and the results showed an 8.2% conversion based on benzene with a selectivity of 8.5% to cyclohexane and 79.2% to cyclohexylbenzene. The CHB/CH (cyclohexylbenzene/cyclohexane) ratio was 9.3 showing the relatively high selectivity of the inventive catalyst for the production of the desired cyclohexylbenzene.

EXAMPLE IV

(A) Catalyst Preparation

A 20 g. sample of 20–30 mesh silica-alumina (Mobil Durabead cracking catalyst) containing about 56 weight percent silica and about 44 weight percent alumina was sprayed with a solution prepared by dissolving 0.0245 g. ruthenium trichloride and 0.2787 g. nickel bromide trihydrate in about 20 ml absolute ethanol and 1 ml water. The catalyst was dried overnight at room temperature. The resulting catalyst was calculated to contain 0.05 weight percent Ru and 0.30 weight percent Ni.

(B) Cyclohexylbenzene Run 4

The stainless steel pipe reactor of Example I was charged with 25 ml of 3 mm Pyrex glass beads, 10 ml (8.5 g.) of the above catalyst and then additional glass beads to fill the reactor to a volume of about 30 ml. The system was pressure checked and the catalyst was treated by maintaining the reactor contents of about 150° C. for 15 minutes under 500 psig hydrogen. Benzene when then pumped into the reactor at a rate of 334 ml/hr (LHSV=34.4) during a reaction period of six hours at about 225° C. and a hydrogen pressure of 500 psig. The gas chromatographic analyses of samples taken over the six hour reaction period were averaged and the results showed and 8% conversion based on benzene with a selectivity of 13.8% to cyclohexane and 78.8% to cyclohexylbenzene. The CHB/CH (cyclohexylbenzene/cyclohexane) ratio for this run was 5.7.

The run described in Example IV above illustrates the process of the present invention on a synthetic silica alumina support at the relatively higher temperature of 225° C.

EXAMPLE V

(A) Catalyst Preparation

A 20 g. sample of a 20–30 mesh catalyst grade silica-alumina, obtained by crushing and sieving extrudates which contained about 87% silica and about 13 weight percent alumina, was sprayed with a solution prepared by dissolving 0.0250 g. ruthenium trichloride and 0.2774 g. nickel bromide trihydrate in about 20 ml absolute ethanol and one milliliter of water. The catalyst was dried overnight at room temperature. The resulting catalyst was calculated to contain 0.05 weight percent Ru and 0.30 weight percent Ni.

(B) Cyclohexylbenzene Run

Into a stainless steel pipe reactor bedded with Pyrex glass beads was charged about 15 ml (7.4 g.) of the above catalyst and additional glass beads were introduced on top of the catalyst to fill the reactor volume. The system was pressure checked, heated to 150° C., and pressured to 500 psig with hydrogen for 15 minutes. During a reaction period of about 3.5 hours, benzene was pumped into the reactor at a rate of about 300 ml/hr (LHSV=20) at a hydrogen pressure of 500 psig and a temperature in the range of 210°–230° C. The gas chromatographic analyses of samples taken over the 3.5 hour reaction period were averaged and the results showed about 9% conversion based on benzene with a selectivity of 31% to cyclohexane and 55% to cyclohexylbenzene. The CHB/CH (cyclohexylbenzene/cyclohexane) ratio for this run was about 1.9. The relatively high conversion and selectivity for this run illustrate the relatively high per-pass yield of desired product utilizing the process of the present invention.

Reasonable variations and modifications, which will be apparent to those skilled in the art, can be made in this invention without departing from the spirit and scope thereof.

What is claimed is:

1. A catalyst for the conversion of monocyclic aromatic and alkyl-substituted monocyclic aromatic hydrocarbons consisting essentially of from about 0.01 to 0.3 weight percent ruthenium, from about 0.03 to 1 weight percent nickel and a support material selected from the group consisting of active clay and synthetic silica-alumina in a weight ratio of ruthenium to nickel in the approximate range of 0.01 to 0.3:1.

2. The catalyst of claim 1 wherein said nickel is present in said catalyst as nickel bromide.

3. The catalyst of claim 1 wherein said support is active clay.

4. The catalyst of claim 1 wherein said support is synthetic silica-alumina.

5. The catalyst of claim 1 wherein said ruthenium is present in said catalyst in an approximate amount ranging from 0.03 to 0.1 weight percent and said nickel is present in said catalyst in an approximate amount ranging from 0.1 to 0.6 weight percent.

6. The catalyst of claim 1 wherein said ratio of ruthenium to nickel is in the approximate range of 0.1:1 to 0.25:1.

* * * * *